United States Patent [19]
McCormick

[11] Patent Number: 5,928,934
[45] Date of Patent: Jul. 27, 1999

[54] APPARATUS AND METHOD FOR PREPARING SMALL TISSUE SAMPLES FOR HISTOLOGICAL EXAMINATION

[76] Inventor: James B. McCormick, 6755 Longmeadow La., Lincolnwood, Ill. 60646

[21] Appl. No.: 09/060,720

[22] Filed: Apr. 14, 1998

[51] Int. Cl.⁶ .................................................. C12M 3/00
[52] U.S. Cl. .................................... 435/284.1; 435/307.1; 425/117
[58] Field of Search .................................... 422/101, 102; 425/117; 435/11, 284.1, 307.1

[56] References Cited

U.S. PATENT DOCUMENTS

| | | | |
|---|---|---|---|
| 5,061,452 | 10/1991 | Yamamoto et al. | 422/101 |
| 5,080,040 | 1/1992 | McCormick | 422/102 |
| 5,424,040 | 6/1995 | Bjornsson | 422/101 |
| 5,427,742 | 6/1995 | Holland | 422/102 |
| 5,543,114 | 8/1996 | Dudek | 422/102 |

*Primary Examiner*—David A. Redding
*Attorney, Agent, or Firm*—Fitch, Even, Tabin & Flannery

[57] ABSTRACT

The present invention is directed to a cassette for use in the preparation of small specimens for histological examination. While the cassette of the present invention is particularly adapted for use with small specimens, it is equally suitable for use in the processing of large specimens. The cassette includes an open container having a bottom wall, two side walls, a front wall and a back wall. The bottom wall has a plurality of first apertures disposed in the wall for passage of fluid through the cassette in a direction orthogonal to the plane of the bottom wall. At least two of the other walls also have a plurality of second apertures for the passage of fluid through the cassette in a direction parallel to the plane of the bottom wall. Each of the back wall, side walls and front wall are disposed at an angle outwardly from the bottom wall. All of the apertures of the cassette bottom, top and inner side walls have a longest dimension no greater than about 0.5 mm. Each of the first apertures and the second apertures can be any suitable shape such as round, oval, square or rectangular so long as the longest dimension of the aperture is less than about 0.5 mm. Another feature of the invention is that the walls comprising the apertures of the bottom wall are disposed at an angle inwardly from the interior floor of the bottom wall.

14 Claims, 2 Drawing Sheets

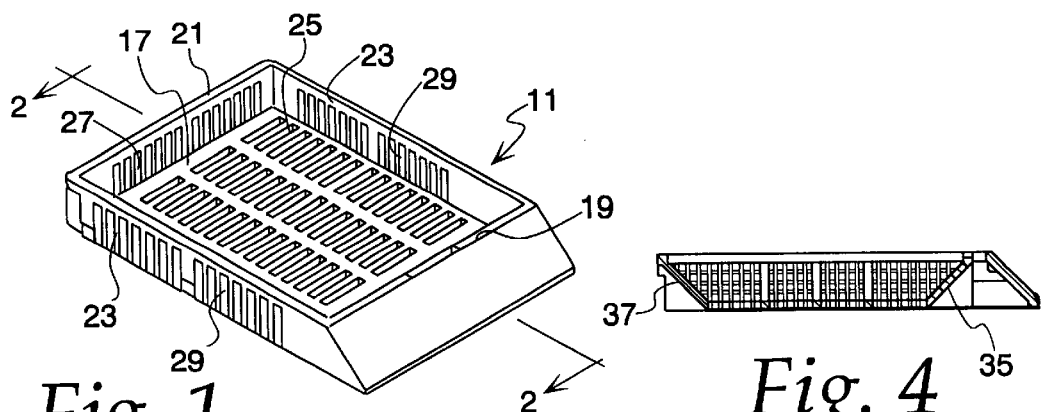
Fig. 1
PRIOR ART
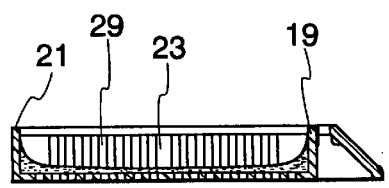
Fig. 2
PRIOR ART
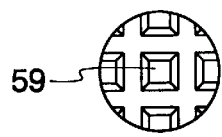
Fig. 4
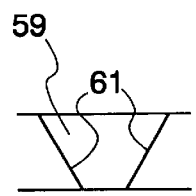
Fig. 5
Fig. 6
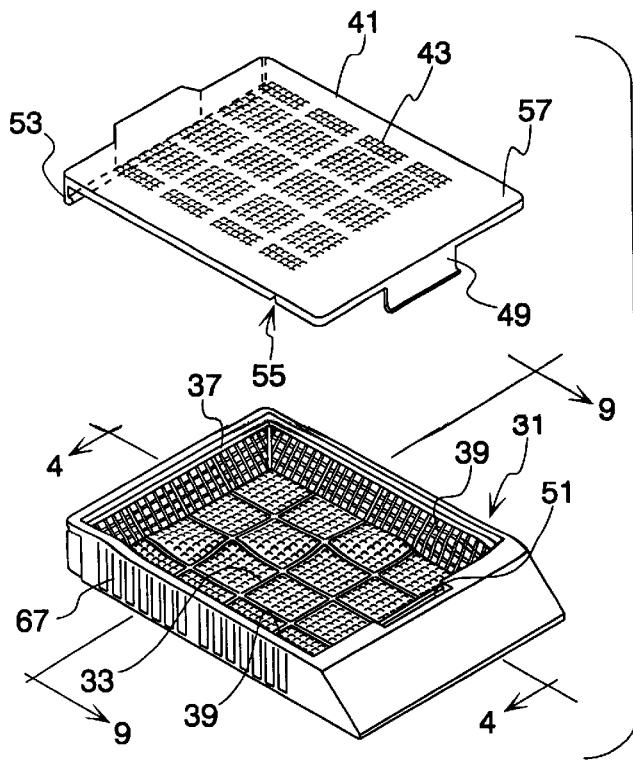
Fig. 3

APPARATUS AND METHOD FOR PREPARING SMALL TISSUE SAMPLES FOR HISTOLOGICAL EXAMINATION

FIELD OF THE INVENTION

The present invention relates to the preparation of small tissue samples for histological examination and more particularly relates to improved methods and apparatus for treatment of small tissue samples prior to embedding the tissue samples in paraffin or the like in preparation for microscopic examination.

BACKGROUND OF THE INVENTION

Standard procedures for preparing tissue samples for microscopic examination involve embedding the tissue sample in paraffin and slicing the paraffin-embedded tissue sample very thinly with a microtome. Prior to embedding the tissue sample, the tissue sample is pretreated in various solutions appropriate to the examination. Typically, prior to paraffin embedding, the tissue sample is fixed, dehydrated, cleared, infiltrated with molten paraffin and, depending on the test, stained. Such prior treatment of the tissue samples requires subjecting the tissue sample to contact with various fluids, including ethanol, xylene, formaldehyde and water.

The trend in histological examination is to take much smaller samples through less invasive techniques. This creates several problems for the histology laboratory. One problem is that currently available processing cassettes have apertures large enough to permit the tissue sample to escape from the cassette during processing. A further problem is that presently available cassettes have right angle walls. During the final treatment of the tissue sample in the cassette, the sample is immersed in molten wax. As the wax begins to harden, the sample is removed from the cassette and placed into the bottom portion of an embedding mold. However, the right angle walls of the present cassettes result in creating a capillary action along the wall which tends to move the sample up the wall. Because of the small size of the sample, the sample can be very difficult to locate in the cassette for removal to the embedding mold.

U.S. Pat. No. 5,080,869 to McCormick is directed to a typical prior art cassette. As shown in FIG. 1 of the McCormick patent, the wall apertures and the bottom apertures are elongated slots having a relatively wide width. The cassette walls are at right angles to the bottom wall.

U.S. Pat. No. 5,269,671 to McCormick also discloses a cassette with slot like apertures and right angle side walls.

Accordingly, it is a principal object of the present invention to provide a cassette for use in the treatment of small tissue specimens for histological examination.

This and other objects of the invention will become more apparent from the following detailed description and the accompanying drawings.

BRIEF DESCRIPTION OF THE DRAWINGS

FIG. 1 is a perspective view of a prior art cassette;

FIG. 2 is a cross-sectional view of the cassette of FIG. 1;

FIG. 3 is a perspective view of the cassette of the invention shown with an accompanying top closure;

FIG. 4 is a cross-sectional view of the cassette of FIG. 3;

FIG. 5 is an enlarged view looking down of several of the apertures located in the bottom of the cassette;

FIG. 6 is an enlarged cross-sectional view of one of the openings in the bottom of the cassette of FIG. 3;

SUMMARY OF THE INVENTION

Figure 7:
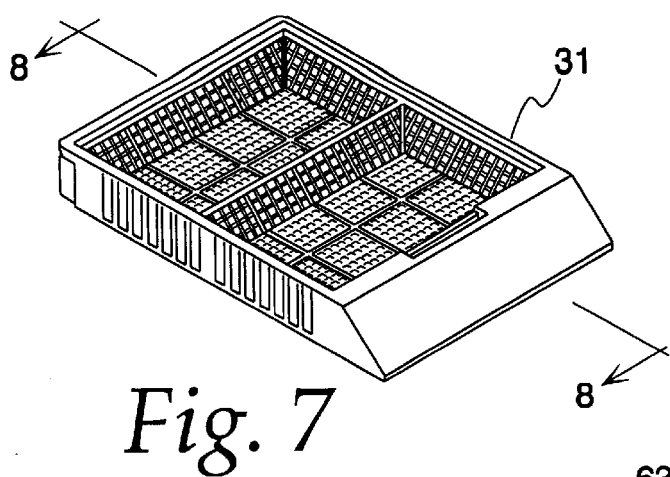
FIG. 7 is a perspective view of another embodiment of a cassette of the invention.

The present invention is directed to a cassette for use in the preparation of small specimens for histological examination. While the cassette of the present invention is particularly adapted for use with small specimens, it is equally suitable for use in the processing of large specimens. The cassette includes an open container having a bottom wall, two side walls, a front wall and a back wall. The bottom wall has a plurality of first apertures disposed in the wall for passage of fluid through the cassette in a direction orthogonal to the plane of the bottom wall. At least two of the other walls also have a plurality of second apertures for the passage of fluid through the cassette in a direction parallel to the plane of the bottom wall. Each of the back wall, side walls and front wall are disposed at an angle outwardly from the bottom wall. All of the apertures of the cassette bottom, top and inner side walls have a longest dimension no greater than about 0.5 mm. Each of the first apertures and the second apertures can be any suitable shape such as round, oval, square or rectangular so long as the longest dimension of the aperture is less than about 0.5 mm. Another feature of the invention is that the walls comprising the apertures of the bottom wall are disposed at an angle inwardly from the interior floor of the bottom wall.

DETAILED DESCRIPTION OF THE INVENTION

As shown in FIG. 1, a prior art cassette 11 comprises a bottom wall 17, a front wall 19, a back wall 21 and two side walls 23. At least two walls selected from the back wall 21, the front wall 19 and the side walls 23 are provided with a plurality of apertures in the shape of elongated slots for passage of fluid through the cassette in a direction parallel to the plane of the bottom wall. Preferably, the selected walls having apertures are opposed walls selected from either the front wall 19 and back wall 21 or the two side walls 23. Most preferably all of the side walls are provided with apertures as shown in FIG. 1. As described in U.S. Pat. No. 5,080,869 to McCormick, the elongated slots in the side walls are disposed at an angle relative to the direction of flow and serve to create a swirling flow within the cassette to better contact the specimen with the fluid being passed through the cassette.

The bottom wall is also provided with a plurality of apertures 25 in the shape of elongated slots. As shown in the embodiment in FIG. 1 and FIG. 2, the back wall 21 and front wall 19 are provided with apertures 27 and both of the side walls 23 and the back wall are provided with apertures 29. As shown in FIGS. 1 and 2, the back wall, the front wall and the two side walls join with the bottom wall at a right angle.

One embodiment of the cassette of the present invention is shown in FIGS. 3 and 4. The cassette 31 has a bottom wall 33, an inner front wall 35, an inner back wall 37 and two inner side walls 39. Each of the bottom wall, the front wall, the back wall and the two side walls are provided with a plurality of small apertures. The apertures are characterized in that the longest dimension of each of the apertures is less than 0.5 mm. The apertures can be any suitable shape, such as round, oval, square or rectangular, so long as the longest dimension of the aperture does not exceed 0.5 mm. The apertures are present in the inner front wall, inner back wall and two inner side walls at a level sufficient to provide from about 40 to about 60% porosity as a percent of the total surface area of the walls. The bottom wall has apertures present at a level sufficient to provide from about 40 to about 60%. porosity as a percentage of the total area of the bottom wall.

A top cover 41 is also provided. The top cover has apertures 43 which also have a longest dimension of 0.5 mm. Preferably, all the apertures in all the walls and the cover are in the shape of a circle having a diameter of about 0.4 mm to about 0.5 mm or a square having a width of from about 0.4 to about 0.5 mm. The cover 41 is provided with a tab 49 which is inserted into the opening 51 in the cassette. Spring tabs 53 are provided which mate with the back wall of the cassette to engage the cover in place when pressed downwardly.

The top cover 41 has a line of weakness formed by providing a notch 55 in the bottom surface of top cover 41 and a diminished line of thinned wall section. The area 57 can then be used as additional area for writing the identification of the specimen placed into the cassette. The area 57 can be broken from top cover 41 and placed into the interior of cassette 31 prior to finishing the embedding process with molten wax.

As shown in FIGS. 3 and 4, the front wall 35, the back wall 37 and the two side walls 39 are disposed at an angle outwardly from the bottom wall 33. The angle is preferably from about 45° to about 50°. The last step in processing of a specimen in cassette 11 and cassette 31 is to treat the specimen with molten wax by pouring molten wax into the bottom of the cassette. In the prior art cassette 11, the molten wax forms a deep meniscus at the junction of the walls with the bottom wall. A small sample can be carried upwardly along the wall and can be difficult for the operator to locate when it is time to transfer the specimen to an embedding mold. The use of the angle walls of the cassette 31 of the present invention eliminates most of the capillary force generated meniscus and makes the job of the operator much easier in locating a small specimen for transfer to the embedding mold.

Figure 8:
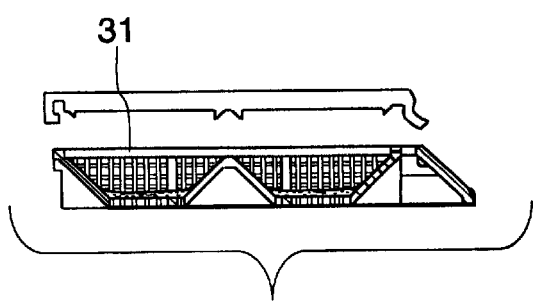
FIG. 8 is a cross-sectional view of the cassette of FIG. 7 showing the cassette after the sample which was processed has been placed in the bottom of a mold and wax has been cast into the mold.
Figure 11:
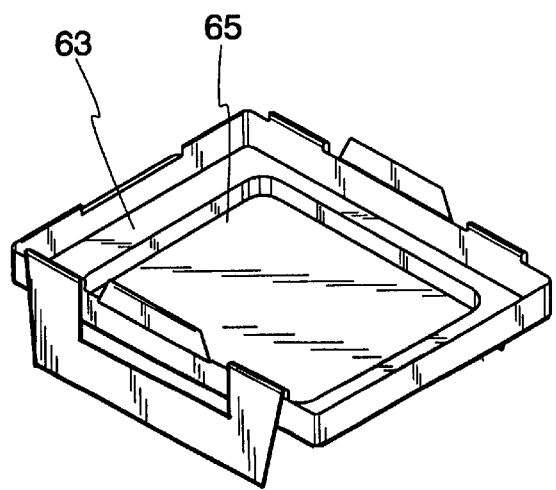
FIG. 11 is a perspective view of an embedding mold.

A further feature of the cassette of the present invention is shown in FIGS. 5 and 6. As seen in the enlarged view of the apertures 59 formed in bottom wall 33, the sides of the aperture 59 have side walls 61 disposed at an angle inwardly from the interior floor of the bottom wall. Because of the smallness of the apertures 59 in bottom wall 33, the cassette could easily be broken from the wax which is used to attach the cassette to the specimen in an embedding mold. The inclined side walls 61 of bottom wall 33 provide a gripping plug of wax as it hardens in the apertures. In operation, the specimen which has been treated is removed from cassette 31 and placed into a bottom chamber 65 of an embedding mold 63 shown in FIG. 11. The specimen is placed in the bottom chamber 65 of the embedding mold. The cassette 31 is placed in the top chamber of the embedding mold and molten wax is poured into the embedding mold through the apertures in the bottom wall 33 of the cassette. After the wax hardens, the specimen is affixed to cassette 33 by means of the wax casting and the cassette 33 can then be clamped in a microtome for taking slices of the specimen. The cassette and wax casting is shown in FIG. 8. The cassette 31 shown in FIG. 8 is a two-section cassette which can be used for processing different specimens at the same time. The cassette could also have 4, 6, 8 or 12 compartments with side walls disposed at an angle for multiple small specimens with matching detail seals on the cover.

Figure 9:
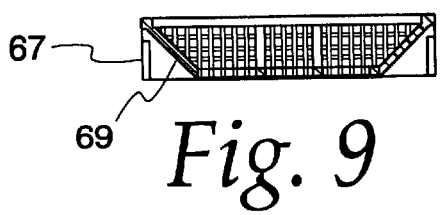
FIG. 9 is a cross-sectional view taken along line 9—9 of FIG. 3.
Figure 10:
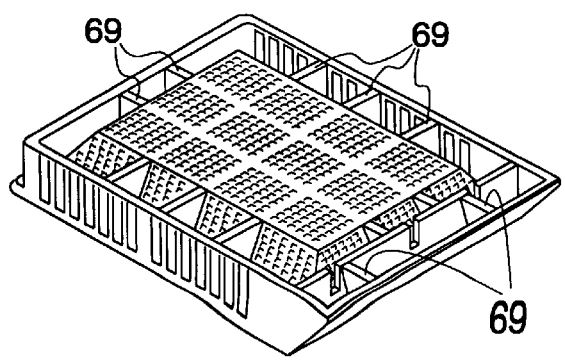
FIG. 10 is a bottom perspective view of the cassette of FIG. 3.

As seen in FIG. 3 and FIG. 9, the cassette 31 is provided with false walls 67. The false walls 67 are provided with elongated slot apertures, which can be angled as described in U.S. Pat. No. 5,080,869 to McCormick. Reinforcing brackets 69 are provided to stabilize the false walls 67. The false walls 67 are not essential and the cassette can merely be provided with the brackets 69 for providing a stable platform for use in operation.

What is claimed is:

1. A histological examination specimen preparation cassette having capillary force-limiting side walls, said cassette comprising;

an open container having a bottom wall, two side walls, a front wall and a back wall;

said bottom wall having a plurality of first apertures disposed therein for passage of fluid through said cassette in a direction orthogonal to the plane of said bottom wall, at least two of said back walls, side walls and front wall having a plurality of second apertures for the passage of fluid through said cassette in a direction parallel to the plane of said bottom wall;

each of said back wall, side walls and front wall being disposed at an angle extending outwardly from said bottom wall, the angle being effective for limiting capillary forces as compared to a cassette having side walls disposed at angles of approximately 90° relative to a bottom wall.

2. A cassette in accordance with claim 1 wherein all of said first apertures and said second apertures have a longest dimension no greater than about 0.5 mm.

3. A cassette in accordance with claim 1 wherein the porosity provided by all of said first apertures and said second apertures is from about 40% to about 60% of the total surface area of said bottom wall, said two side walls, said front wall and said back wall.

4. A cassette in accordance with claim 1 wherein said angle of said walls is from about 5° to about 50° outwardly from a vertical plane.

5. A cassette in accordance with claim 1 wherein said bottom wall apertures have side walls disposed at an angel inwardly from the interior floor of said bottom wall.

6. A cassette in accordance with claim 5 wherein said angle of said aperture side walls is from about 5° to about 50° inwardly from a vertical plane.

7. A cassette in accordance with claim 1 wherein all of said first apertures and said second apertures have a shape selected from the group consisting of circles, squares and rectangles.

8. A cassette in accordance with claim 1 wherein a plurality of compartments is provided, each of said compartments having side walls disposed at an angle outwardly from said bottom wall.

9. A cassette in accordance with claim 8 wherein the number of compartments is from 2 to 12.

10. A cassette in accordance with claim 1 wherein said cassette further comprises a cover.

11. A cassette in accordance with claim 10 wherein said cover has a plurality of apertures.

12. A cassette in accordance with claim 11 wherein said apertures have a longest dimension no greater than about 0.5 mm.

13. A cassette in accordance with claim 10 wherein said cover has a plurality of tabs for engagement with said cassette to secure said cover to said cassette.

14. A cassette in accordance with claim 10 wherein said cover has a notch extending across said cover to allow cleaving of said cover along said notch.

* * * * *

UNITED STATES PATENT AND TRADEMARK OFFICE
CERTIFICATE OF CORRECTION

PATENT NO. : 5,928,934
DATED : July 27, 1999
INVENTOR(S) : James B. McCormick

It is certified that error appears in the above-identified patent and that said Letters Patent is hereby corrected as shown below:

IN THE CLAIMS:
    Claim 5, column 4, line 39, change "angel" to --angle--.

Signed and Sealed this

Eleventh Day of April, 2000

Attest:

Q. TODD DICKINSON

*Attesting Officer*   *Director of Patents and Trademarks*

UNITED STATES PATENT AND TRADEMARK OFFICE
CERTIFICATE OF CORRECTION

PATENT NO. : 5,928,934
APPLICATION NO. : 09/060720
DATED : July 27, 1999
INVENTOR(S) : James B. McCormick It is certified that error appears in the above-identified patent and that said Letters Patent is hereby corrected as shown below:

On Title Page, Item (56)
References Cited, U.S. Patent Documents:

5,080,040  1/1992  McCormick should be 5,080,869  1/1992  McCormick

Signed and Sealed this

Eighth Day of August, 2006

JON W. DUDAS
*Director of the United States Patent and Trademark Office*